United States Patent
Shipp

(10) Patent No.: US 8,282,670 B2
(45) Date of Patent: Oct. 9, 2012

(54) SURGERY DELIVERY DEVICE AND MESH ANCHOR

(75) Inventor: John I. Shipp, Jacksonville Beach, FL (US)

(73) Assignee: Tyco Healthcare Group LP, Mansfield, MA (US)

( * ) Notice: Subject to any disclaimer, the term of this patent is extended or adjusted under 35 U.S.C. 154(b) by 176 days.

(21) Appl. No.: 12/840,509

(22) Filed: Jul. 21, 2010

(65) Prior Publication Data

US 2010/0312258 A1    Dec. 9, 2010

Related U.S. Application Data

(62) Division of application No. 10/709,297, filed on Apr. 27, 2004, now Pat. No. 7,758,612.

(51) Int. Cl.
*A61B 17/08* (2006.01)

(52) U.S. Cl. .................. 606/219; 623/23.72

(58) Field of Classification Search .......... 606/139, 606/151, 213, 219, 304; 623/23.72; 600/142
See application file for complete search history.

(56) References Cited

U.S. PATENT DOCUMENTS

| | | |
|---|---|---|
| RE28,932 E | 8/1976 | Noiles et al. |
| 4,204,541 A | 5/1980 | Kapitanov |
| 4,824,865 A | 4/1989 | Bowser et al. |
| 4,884,572 A | 12/1989 | Bays et al. |
| 4,895,148 A | 1/1990 | Bays et al. |
| 4,976,715 A | 12/1990 | Bays et al. |
| 5,059,206 A | 10/1991 | Winters |
| 5,163,343 A | 11/1992 | Gish |
| 5,169,400 A | 12/1992 | Muhling et al. |
| 5,203,864 A | 4/1993 | Phillips |
| 5,259,398 A | 11/1993 | Vrespa |
| 5,290,297 A | 3/1994 | Phillips |
| 5,354,292 A | 10/1994 | Braeuer et al. |
| 5,582,616 A | 12/1996 | Bolduc et al. |
| 5,643,320 A | 7/1997 | Lower et al. |
| 5,730,744 A | 3/1998 | Justin et al. |
| 5,810,882 A | 9/1998 | Bolduc et al. |

(Continued)

FOREIGN PATENT DOCUMENTS

EP    0 121 362 A1    10/1984

(Continued)

OTHER PUBLICATIONS

International Search Report corresponding to European Application no. Ep 08 00 4478, date of mailing is May 16, 2008; date of completion is mailed May 2, 2008; 8 pages.

(Continued)

*Primary Examiner* — Victor Nguyen

(57) ABSTRACT

A delivery device for delivering a plurality of individual surgical anchors is disclosed. The delivery device includes a housing, a delivery tube, having a distal and a proximal end, an actuator, flexible anchor reaction members, a reciprocating anchor carrier, having a distal and a proximal end, the distal end terminating in a tissue penetrator. The device further includes at least one surgical anchor located in juxtaposition with the anchor carrier. Each of the surgical anchors has a penetration section and a head section. The surgical anchors are preferably made from an absorbable polymer. The actuator is connected to the anchor carrier and has at least two states. The first/home state, includes a position such that the surgical anchor is proximal the distal end of the tube. The second state is such that the penetrating section of the surgical anchor is exposed beyond the distal end of the delivery tube.

13 Claims, 10 Drawing Sheets

U.S. PATENT DOCUMENTS

| | | | |
|---|---|---|---|
| 5,824,008 | A | 10/1998 | Bolduc et al. |
| 5,830,221 | A * | 11/1998 | Stein et al. ............ 606/157 |
| 5,891,146 | A | 4/1999 | Simon et al. |
| 5,954,722 | A | 9/1999 | Bono |
| 5,964,772 | A | 10/1999 | Bolduc et al. |
| 5,971,985 | A | 10/1999 | Carchidi et al. |
| 6,030,162 | A | 2/2000 | Huebner |
| 6,096,060 | A | 8/2000 | Fitts et al. |
| 6,296,656 | B1 | 10/2001 | Bolduc et al. |
| 6,306,140 | B1 | 10/2001 | Diddiqui |
| 6,319,270 | B1 | 11/2001 | Grafton |
| 6,425,900 | B1 | 7/2002 | Knodel et al. |
| 6,447,524 | B1 | 9/2002 | Knodel et al. |
| 6,533,454 | B1 | 3/2003 | Kaikkonen et al. |
| 6,551,333 | B2 * | 4/2003 | Kuhns et al. ............ 606/151 |
| 6,562,051 | B1 | 5/2003 | Bolduc et al. |
| 6,572,626 | B1 | 6/2003 | Knodel et al. |
| 6,692,506 | B1 | 2/2004 | Ory et al. |
| 6,747,121 | B2 | 6/2004 | Gogolewski |
| 6,773,438 | B1 | 8/2004 | Knodel et al. |
| 6,884,248 | B2 | 4/2005 | Bolduc et al. |
| 6,955,677 | B2 | 10/2005 | Dahners |
| 2001/0004694 | A1 | 6/2001 | Carchidi |
| 2001/0007074 | A1 | 7/2001 | Strobel et al. |
| 2002/0004660 | A1 | 1/2002 | Henniges et al. |
| 2002/0013605 | A1 | 1/2002 | Bolduc et al. |
| 2003/0036755 | A1 | 2/2003 | Ginn |
| 2003/0099102 | A1 | 5/2003 | Duval |
| 2003/0135226 | A1 | 7/2003 | Bolduc et al. |
| 2004/0073218 | A1 | 4/2004 | Dahners |
| 2004/0098045 | A1 | 5/2004 | Grafton et al. |
| 2004/0153101 | A1 | 8/2004 | Bolduc et al. |
| 2004/0204723 | A1 | 10/2004 | Kayan |
| 2004/0254608 | A1 | 12/2004 | Huitema et al. |
| 2005/0171562 | A1 | 8/2005 | Criscuolo et al. |
| 2005/0267478 | A1 | 12/2005 | Corradi et al. |
| 2006/0124688 | A1 | 6/2006 | Racenet et al. |
| 2006/0273135 | A1 | 12/2006 | Beetel |
| 2006/0291981 | A1 | 12/2006 | Viola et al. |
| 2008/0097523 | A1 | 4/2008 | Bolduc et al. |

FOREIGN PATENT DOCUMENTS

| | | |
|---|---|---|
| EP | 0 199 037 A2 | 10/1986 |
| EP | 1 025 803 A1 | 8/2000 |
| EP | 1 293 168 A2 | 3/2003 |
| FR | 2 299 548 | 8/1976 |
| FR | 2 377 796 | 8/1978 |
| JP | 09149906 A | 6/1997 |
| WO | WO 98/11814 A2 | 3/1998 |
| WO | WO 01/62136 A2 | 8/2001 |
| WO | WO 01/97677 A2 | 12/2001 |
| WO | WO 02/30296 A2 | 4/2002 |
| WO | WO 02/091932 A1 | 11/2002 |
| WO | WO 03/034925 A2 | 5/2003 |
| WO | WO 03/049906 A1 | 6/2003 |
| WO | WO 03/103507 A2 | 12/2003 |

OTHER PUBLICATIONS

International Search Report corresponding to European Application No. EP 04 75 5078, date of mailing is Jul. 2, 2008; date of completion is Jun. 20, 2008; 7 pages.

International Search Report corresponding to European Application No. EP 08 25 1988, date of mailing is Oct. 17, 2008; completion is Sep. 19, 2008; 8 pages.

International Search Report corresponding to European Application No. EP 08 02 1125, date of mailing is Mar. 16, 2009; date of completion is Mar. 9, 2009; 6 pages.

* cited by examiner

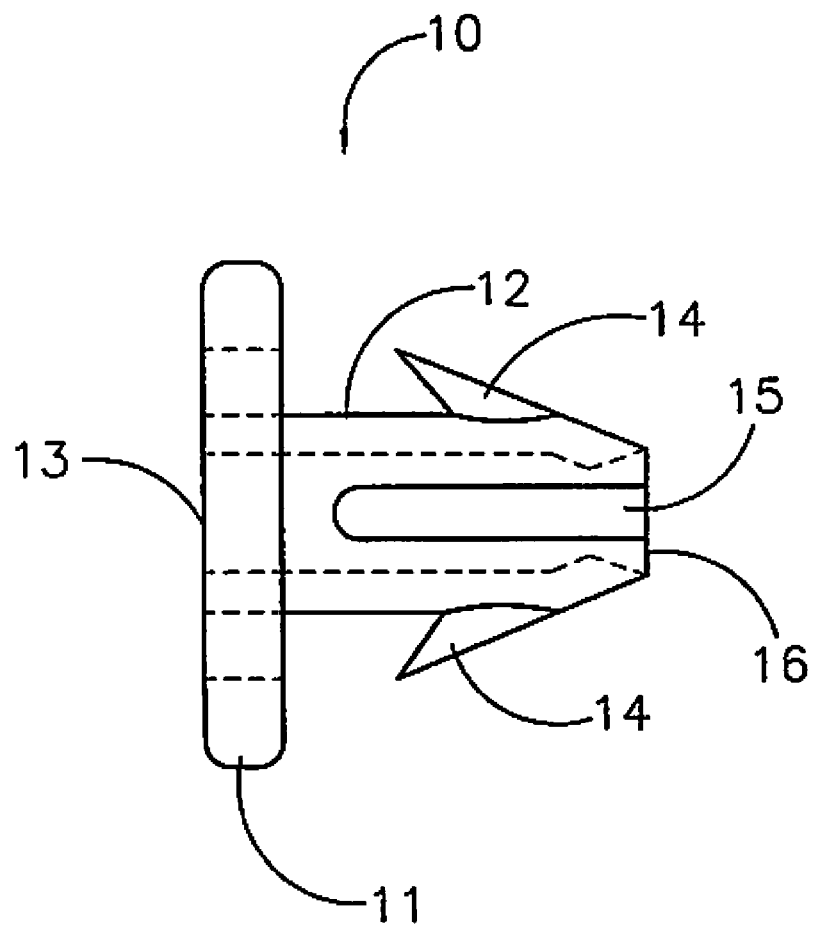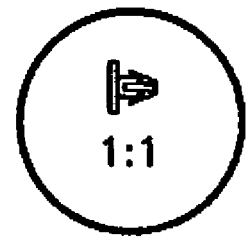
FIG. 1

SURGERY DELIVERY DEVICE AND MESH ANCHOR

CROSS-REFERENCE TO RELATED APPLICATIONS

The present application is a Divisional Application which claims the benefit of and priority to U.S. patent application Ser. No. 10/709,297, filed on Apr. 27, 2004, the entire content of which is incorporated herein by reference.

An inguinal hernia is formed when small a loop of bowel or intestine protrudes through a weak place or defect within the lower abdominal muscle wall or groin. This condition is rather common, particularly in males. Hernias of this type can be a congenital defect or can be caused by straining or lifting heavy objects. The protrusion results in an unsightly bulge in the groin area often causing pain, reduced lifting ability, and in some cases, impaction of the bowel.

Surgery is a common solution to this problem. The preferred surgical technique requires extracting the bowel from the defect, placing a surgical prosthesis such as a mesh patch over the open defect, and attaching the mesh patch to the inguinal floor with conventional sutures or with surgical fasteners or anchors. The repair is accomplished using either open or laparoscopic surgery. Surgical anchors are routinely used in the laparoscopic procedures owing to the difficulty in suturing under laparoscopic conditions.

At present, there are a variety of surgical devices and fasteners available for the surgeon to use in endoscopic or open procedures to attach the mesh patch to the inguinal floor. One such mesh attachment instrument uses a helical wire fastener formed in the shape of a helical compression spring. Multiple helical wire fasteners are stored serially within the 5 mm shaft, and are screwed or rotated into the mesh and the overlaid tissue to form the anchor for the prosthesis. A load spring is used to bias or feed the plurality of helical fasteners distally within the shaft. A protrusion extends into the shaft, while preventing the ejection of the stack of fasteners by the load spring, allows passage of the rotating fastener. U.S. Pat. Nos. 5,582,616 and 5,810,882 by Lee Bolduc, and 5,830,221 by Jeffrey Stein describe instruments and fasteners of this type.

U.S. Pat. Nos. 5,203,864 and 5,290,297 by Phillips describe two embodiments of a hernia fastener and delivery devices. One of the Phillips fasteners is formed in the shape of a unidirectional dart with flexible anchor members. The dart is forced through the mesh and into tissue by a drive rod urged distally by the surgeon's thumb. The anchor members are forced inward until the distal end of the dart penetrates the overlaid tissue and then the anchor members, presumably, expand outward forming an anchor arrangement. Multiple darts are stored in a rotating cylinder, much like a revolver handgun. Phillips second fastener embodiment is a flexible H shaped device. The tissue penetrating means is a hollow needle containing one of the legs of the H. The H shape is flattened with the cross member and the other leg remaining outside the hollow needle owing to a longitudinal slot therein. A drive rod urged distally by the surgeon's thumb again delivers the fastener. The contained leg of the H penetrates the mesh and tissue. After ejection the fastener presumably returns to the equilibrium H shape with one leg below the tissue and one leg in contact with the mesh with the cross member penetrating the mesh and the tissue, similar to some plastic clothing tag attachments.

A series of U.S. Pat. Nos. 6,572,626, 6,551,333, 6,447,524, and 6,425,900 and patent applications 200200877170 and 20020068947 by Kuhns and Kodel, all assigned to Ethicon, describe a super elastic, or shape metal fastener and a delivery mechanism for them. The fasteners are stored in the delivery device in a smaller state and upon insertion into the mesh and tissue transitions to a larger anchor shaped state owing to warming above the super elastic transition temperature from body heat. The Ethicon fastener is delivered by an elaborate multistage mechanism through a hollow needle that has penetrated the mesh and the tissue. The hollow needle is then retracted to leave the fastener to change shape, owing to the temperature transition, to a more suitable configuration for holding the mesh in place.

There are several problems associated with the prior art. The method of penetration of the helical fastener is the same as a wood screw, for example, in that the rotational thread action provides mechanical advantage for the advancement of the fastener through the mesh and tissue. The helical fastener, however, does not have a head or stop on the proximal end so that it can often be screwed all the way through the mesh and into the tissue and thus providing no fastening support for the mesh. As with any screw a pointed distal end is required to cause the screw to start into the material. This configuration can cause permanent pain for some placements of the fastener and sometimes results in the need for the fastener to be excised from the body in a subsequent surgical procedure.

Both the Phillips dart and H shape fastener must be placed in soft enough tissue that will allow the anchor members to deploy or else the holding strength is severely compromised.

The Ethicon device is very complex and expensive to manufacture owing to the delivery mechanism and the cost of the super elastic fastener material. In addition the proximal end of the fastener is not symmetric so that care must be taken to orient it correctly so that both proximal leg members contact the mesh, since fasteners are almost always deployed near the edges of the mesh. Another problem with the Ethicon device is that the delivery tube is 5 mm in diameter and the surgeon must hold a counter force with the palm of the hand on the handle to hold the delivery tube against the mesh while simultaneously applying an oppositely directed force to the trigger (actuator) with his fingers of the same hand. The trigger is spring-loaded and requires a substantially larger force than the tissue penetrating force. These forces change throughout the actuator stroke as the spring loads increase. In addition, the penetrating force peaks then suddenly decreases as the initial penetration is made. These two dynamic countervailing force requirements from the same hand sometimes causes the surgeon to apply too much handle pressure resulting in the 5 mm delivery tube puncturing the tissue causing excess bleeding and other trauma.

The distal end of the dart, the helical coil, and the shape metal fasteners are all pointed shaped and often twenty or more fasteners are used in a single case so that there are many sharply pointed fasteners that are implanted in the groin area. These fasteners can touch or penetrate nerves and cause severe pain that is more or less permanent unless they are removed in subsequent surgical procedures.

What is needed then is a hernia mesh fastener or anchor that is simple to deploy, does not have an implanted sharp distal point, and preferably is absorbed by the body after a period of time when the tissue in-growth to the mesh obviates the need for a fastener or anchor.

What is further needed is a simple inexpensive hernia mesh anchor deployment device that does not require simultaneous dynamic countervailing force to be applied by the same hand of the surgeon.

SUMMARY OF INVENTION

A delivery device for delivering a plurality of individual surgical anchors is disclosed. The delivery device comprises a housing, a delivery tube, having a distal and a proximal end, an actuator, flexible anchor reaction members, a reciprocating anchor carrier, having a distal and a proximal end and a distal and proximal position, the distal end terminating in a tissue penetrator. The device further includes at least one surgical anchor located in juxtaposition with the anchor carrier and a queuing spring to urge the anchors distally. Each of the surgical anchors has a penetration section and a head section. The surgical anchors are preferably made from an absorbable polymer. The actuator is connected to the anchor carrier and has at least two states. The first, or home state, comprises a position such that the surgical anchor is proximal the distal end of the delivery tube. The second state is such that the penetrating section of the surgical anchor is exposed beyond the distal end of the delivery tube. The anchor of the present invention is then deployed by simply applying a distal force to the handle of the housing and penetrating the prosthesis and tissue. A reaction member formed inside and affixed to the delivery tube provides a stop against which the reaction force of penetration is applied to the head section of the anchor. When the surgeon is ready to deploy the anchor a trigger is held stationary against the handle such that no dynamic countervailing forces are encountered. The anchor has a centered internal channel through which the cylindrical anchor carrier passes. The distal penetrating tip of the an-chor carrier is shaped like a conical arrowhead with a proximate step-up in diameter from the anchor carrier cylinder. The inside diameter of the distal end of the an-chor closely matches the carrier cylinder diameter but al-lows for an easy slip fit. The proximate step-up at the penetrating tip serves as a distal stop for the anchor against the force of the queuing spring. The penetration section of the anchor is then forced through the pros-the-sis and tissue. The head of the anchor engages the prosthesis and thus provides a stop that does not allow the anchor to traverse the prosthesis as sometimes happens in the use of the helical fastener. The anchor of the present invention is equipped with rigid radial tissue en-gagement barbs. As the penetration section penetrates the tissue the rigid barbs expand the tissue to allow the section to pass into the tissue. As the proximal end of the barbs enters the tissue the expanded tissue retracts to the diameter of the penetrating section shaft thus locking the anchor in place much like an arrowhead. Unlike the flexi-ble Phillips anchor members the rigid barbs of the present invention will not collapse in rigid tissue. The Phillips members will remain collapsed in rigid tissue thus offer-ing little or no holding strength. After the anchor of the current invention is inserted to the head depth the surgeon releases the trigger and a restoring torsion spring places a proximal force on the anchor carrier, the distal end of the penetrating shaft of the anchor expands owing to distal longitudinal slits such that the tissue penetrator member retracts leaving the anchor in place. The process is then repeated for the next anchor.

BRIEF DESCRIPTION OF DRAWINGS

The novel features of the invention are set forth in the appended claims. The invention itself, however, both as to organization and methods of operation, together with further objects and advantages, may best be understood by reference to the following description, taken in conjunction with the accompanying drawings in which:

FIG. 1 is a side view of the surgical anchor of the present invention.

DETAILED DESCRIPTION

The present invention relates to a surgical device and, more particularly, to a surgical device for serially deploying at least one surgical anchor from a surgical device to attach a prosthesis in place in the repair of a defect in tissue such as an inguinal hernia.

The present invention is illustrated and described in conjunction with a repair of an inguinal hernia, by way of example, however, it should be understood that the present invention is applicable to various other surgical procedures that require the repair of defects in tissue.

The Anchor

Figure 2:
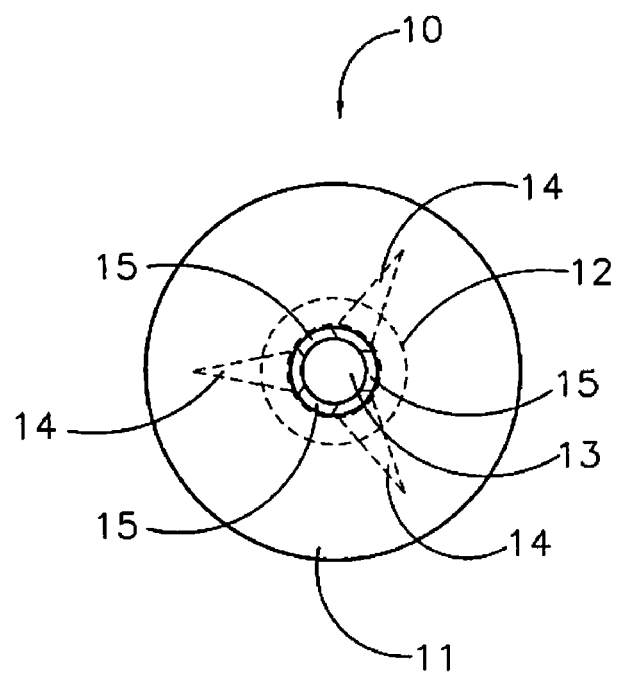
FIG. 2 is the distal end view of the surgical anchor of the present invention.
Figure 3:
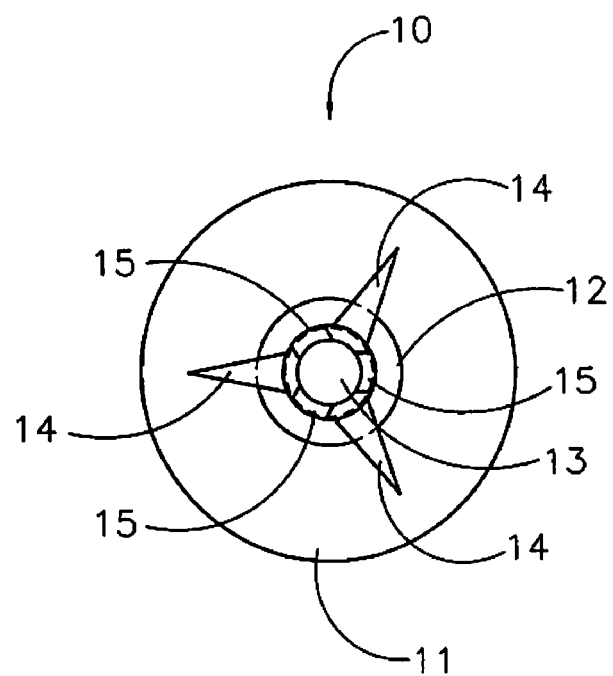
FIG. 3 is the proximal end view of the surgical anchor of the present invention.

Referring to FIGS. 1, 2, and 3, the anchor of the present invention is generally designated by the number 10. Anchor 10 comprises a penetration shaft section 12, a head 11, and three rigid barbs 14. Internal channel 13 is concentric with the longitudinal axis and three slits 15 are equally spaced around penetration shaft 12. The distal end of anchor 10 is designated 16. Penetration shaft 12 is tapered from the distal most point on barbs 14 to distal end 16. Distal end 16 is blunt. Anchor 10 is preferably formed from a bio-absorbable material that has a lifetime after implantation of from 2 to 12 months. Barbs 14 are rigid and are formed integral to the penetration shaft 14. Slits 15 in distal end 16 of penetration shaft 12 allow distal end 16 to flex to facilitate ejection of anchor 10 from the delivery device, which is described in more detail below. The general dimensions of the anchor are: head diameter, 5 mm; penetration shaft diameter 3 mm; overall length 5 mm.

The Delivery Device

Figure 4:
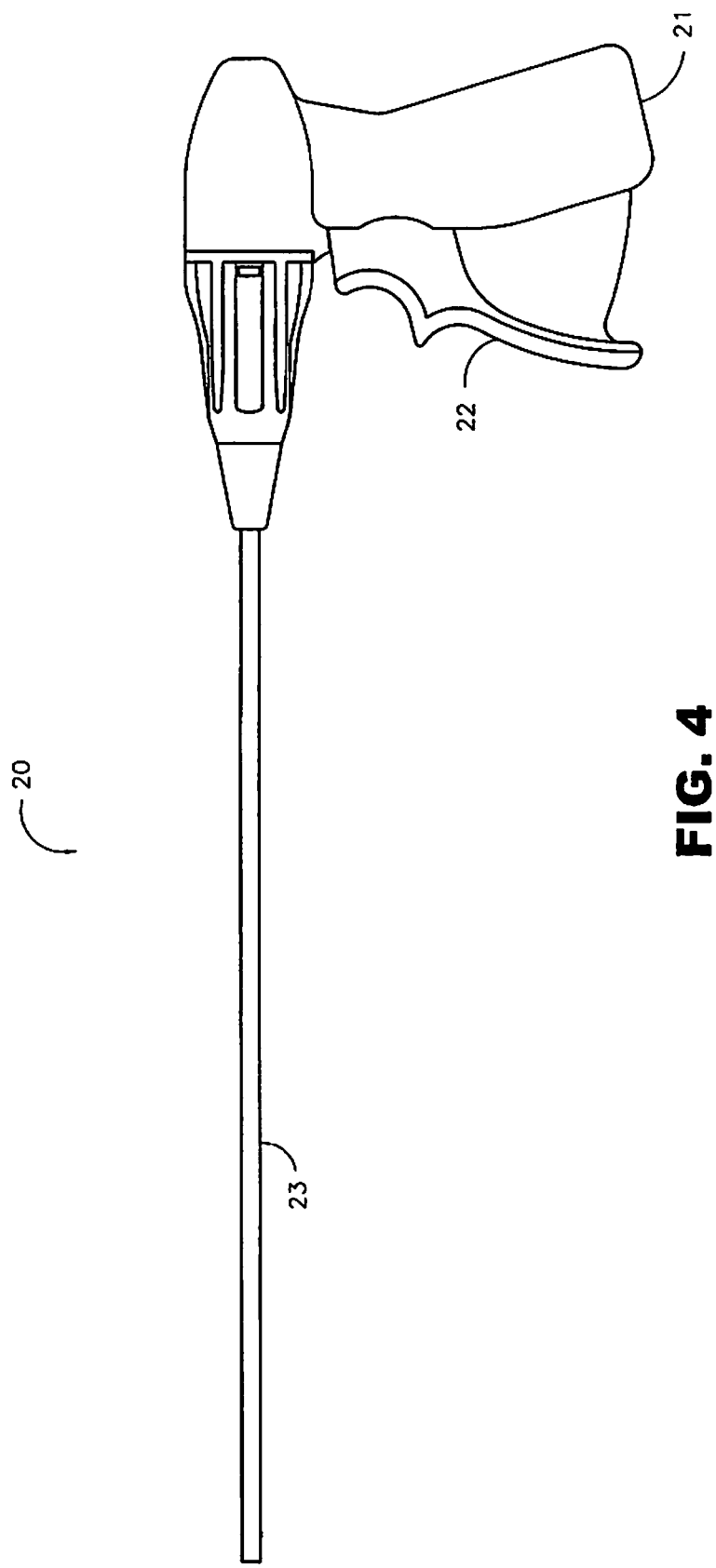
FIG. 4 is a side view of the anchor delivery device.
Figure 5:
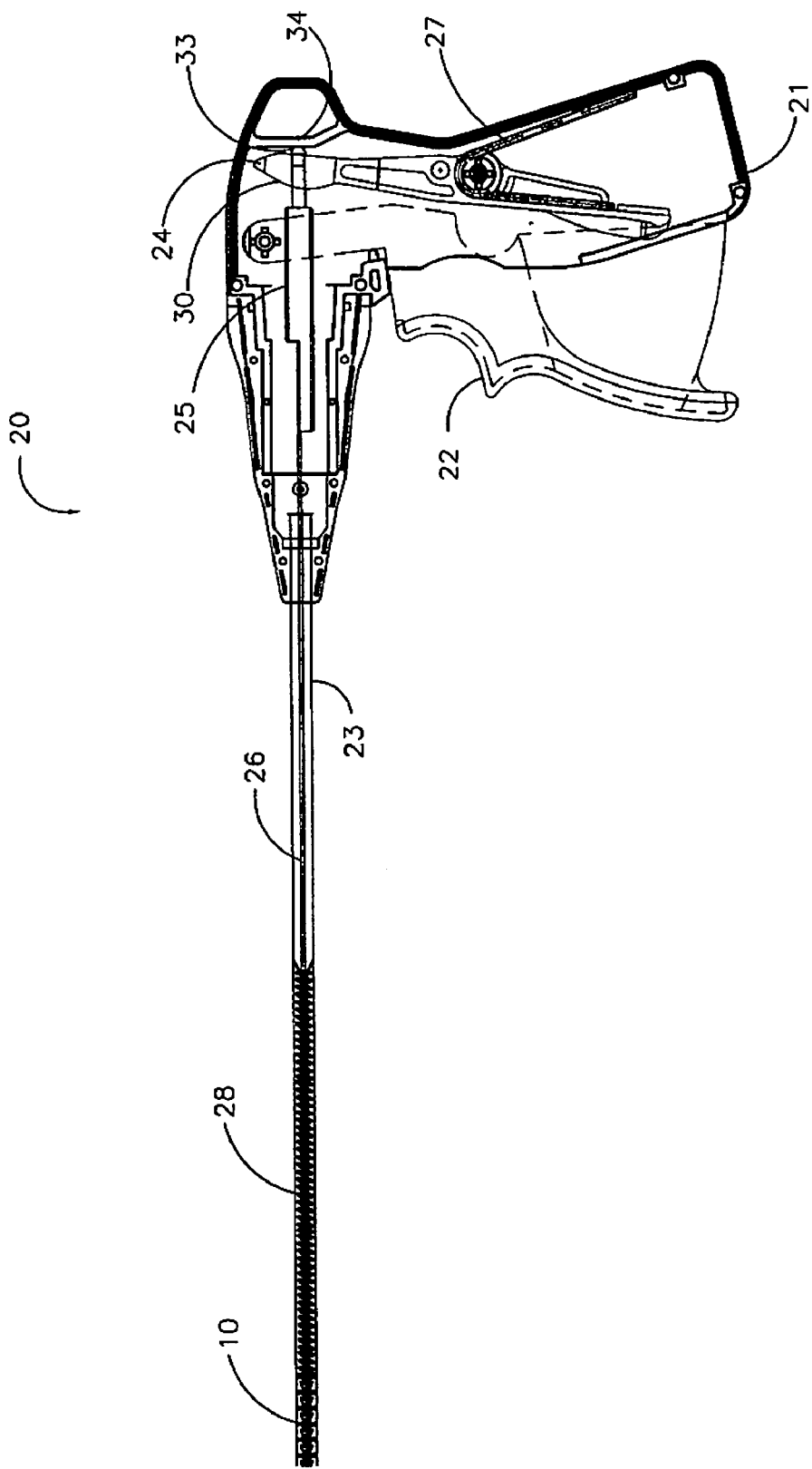
FIG. 5 is a cross section of the anchor delivery device in the home state.

The deliver device can be best understood by referring to FIGS. 4-8. FIG. 4 depicts a side view of the delivery device, generally designated with the number 20. Delivery device 20 comprises pistol grip handle 21, an actuator or trigger 22 and delivery tube 23. The outside diameter of delivery tube 23 is, preferably, approximately 5 mm for use with standard trocars, laparoscopic devices for minimally invasive entry into the abdomen. Handle 21 and trigger 22 are preferably formed from plastic material such as ABS or polycarbonate but alternately can be formed from metal to facilitate reuse and resterilization. Delivery tube 23 is preferably formed from thin wall stainless steel but can alternately be formed from rigid biocompatible plastic material. As can be seen in FIG. 5 delivery tube 23 contains multiple anchors 10. Delivery tube 23 can be designed so that it is readily detachable from handle 21 thus resulting in a reusable handle and a reloadable or replaceable tube, otherwise the entire delivery device is for use only in a single surgical procedure.

Figure 7:
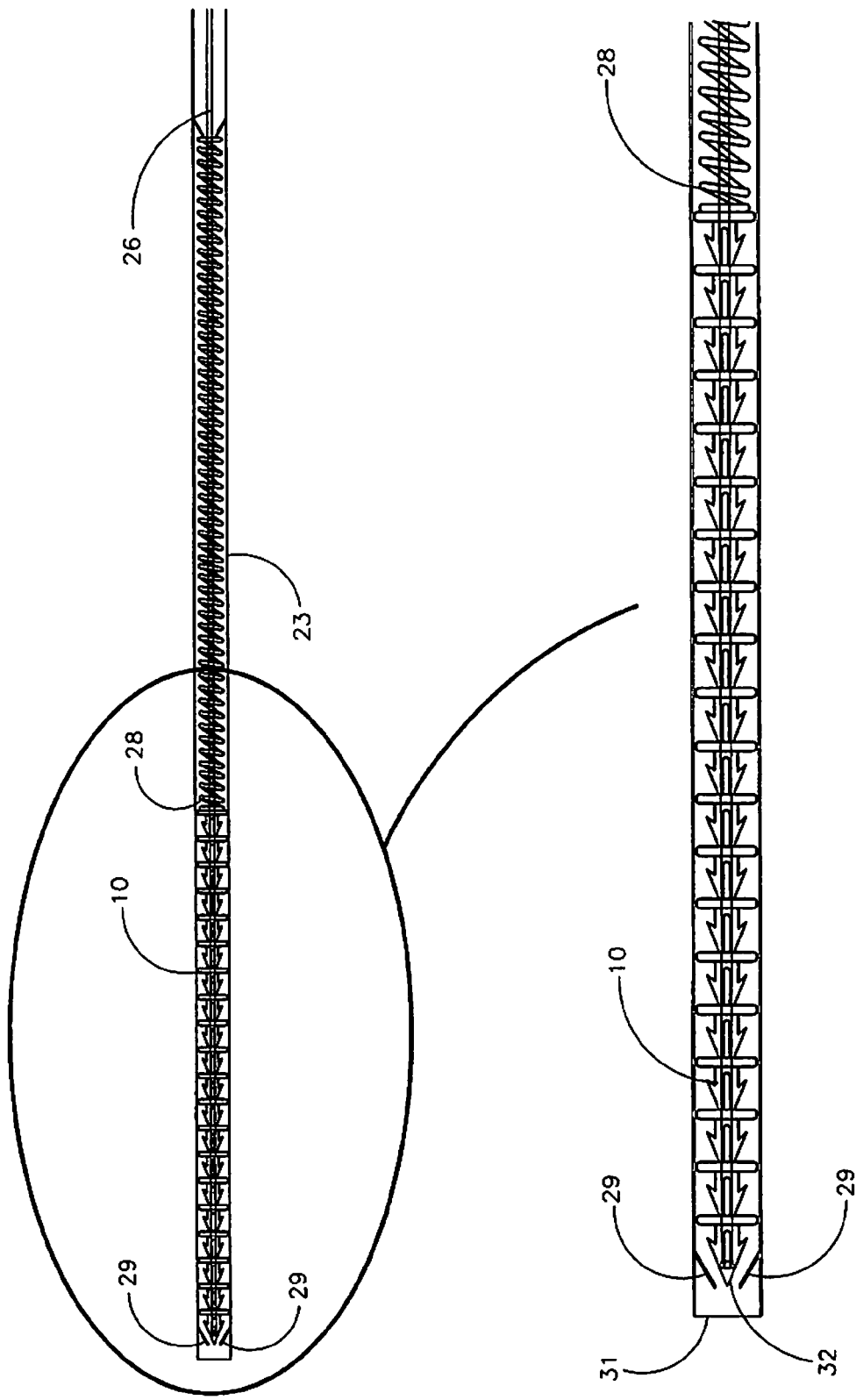
FIG. 7 is a cross section of the distal end of the delivery device in the home state.

FIGS. 5 and 7 are longitudinal cross sections of the proximal and distal ends respectively of delivery device 20 in the home or equilibrium state. Trigger 22 abuts rotating lever 24 which is spring loaded with torsion spring 27. Anchor carrier 26, connected proximally to piston 25, comprises a cylindrical rod terminating distally in tissue penetrator member or tissue penetrator 32. Anchors carrier 26 is fed inside internal channels 13 of anchors 10 such that anchors 10 are in head 11—to distal end 16—contact such that distal ends 16 of anchors 10 are aligned toward distal end 31 of delivery device 20. The proximal end of queuing spring 28 is fixed with respect to delivery tube 23 and the distal end of queuing spring 28 abuts head 11 of proximal-most anchor 10. Queuing spring 28 is compressed and serves to urge anchors 10 distally against each other and against the proximal shoulder of tissue penetrator 32 that abuts distal end 16 of distal-most anchor 10 and provides a counter force against queuing spring 28. Distal end 16 of anchor 10 and the proximal end of tissue penetrator 32 are each formed such that there is a smooth transition between the two components. This minimizes the insertion force required to set anchor 10 into the prosthesis and tissue. With anchor carrier 26 fully loaded with a plurality of anchors the reaction force of queuing spring 28 is sized such that it is inadequate to spread slots 15 of distal most-anchor 10. This assures containment of distal-most anchor 10 inside delivery tube 23 when delivery device 20 is in the home state as depicted in FIGS. 5 and 7.

Figure 6:
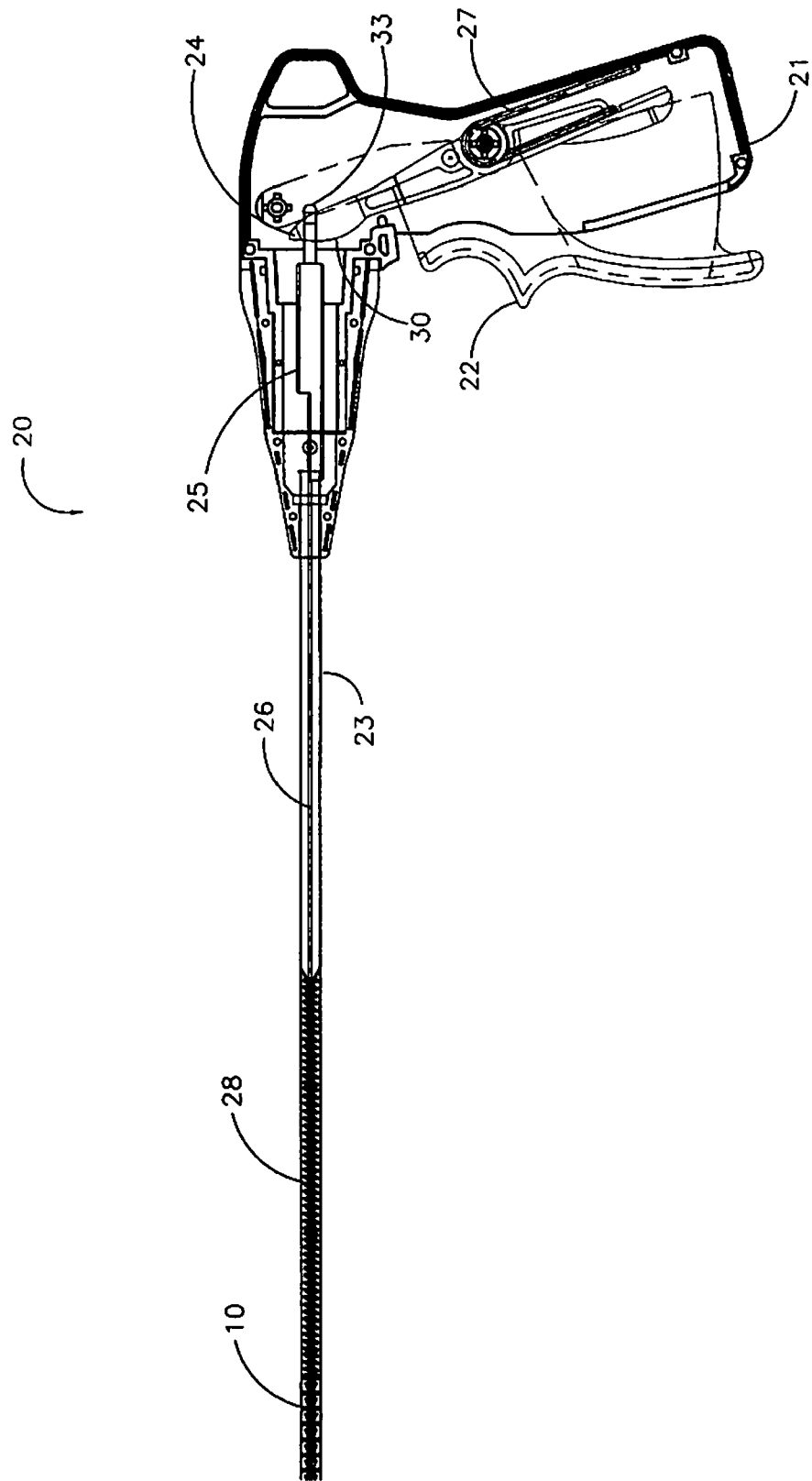
FIG. 6 is a cross section of the anchor delivery device in the stroked state.
Figure 8:
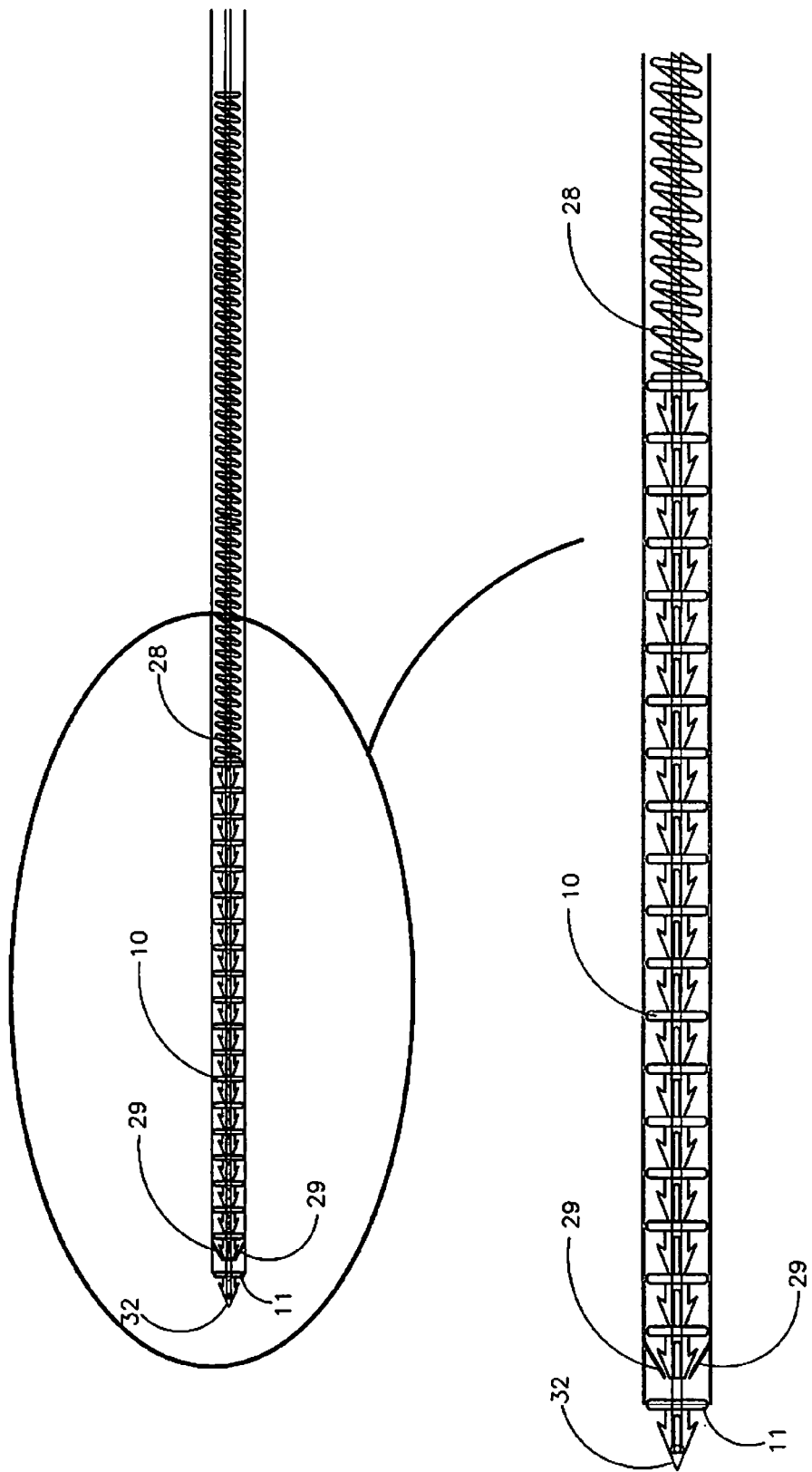
FIG. 8 is a cross section of the distal end of the delivery device in the stroked state.

Referring now to FIGS. 6 and 8, when the surgeon pulls trigger 22 proximally, away from the home state, lever 24 rotates counterclockwise such that cam surface 30 of lever 24 contacts piston 25 which drives anchor carrier rod 26 distally. Torsion spring 27 compresses as lever 24 is rotated counterclockwise. Anchor carrier 26 is urged distally within the inside diameter of queuing spring 28. FIGS. 6 and 8 depict delivery device 20 in the fully stroked state. In this state head 11 of distal-most anchor 10 has been urged past flexible reaction members 29 that are fixed with respect to delivery tube 23 and penetration shaft 12 of distal-most anchor 10 is exposed past the distal end 31 of delivery tube 23. In this fully stroked state trigger 22 is locked to handle 21 by the surgeon's closed hand and no further activation of deliver device 20 is necessary to set the anchor into the prosthesis and tissue. Thus no countervailing dynamic forces are required from a single hand of the surgeon. Simply the surgeon gently pushing the entire assembly distally then sets distal-most anchor 10. Tissue penetrator 32 leads distal-most anchor 10 into the prosthesis and the tissue until penetration shaft 12 fully engages and head 11 stops against the prosthesis. Flexible reaction members 29 counter the insertion force of distal-most anchor 10 so that anchors 10 do not move proximal during insertion.

Barbs 14 lock distal-most anchor 10 into the tissue. Distal-most anchor 10 is then ejected from delivery device 20 when the surgeon retracts delivery device 20 proximally. Slits 15 spread open allowing penetrator 32 to pass through internal channel 13, thus releasing distal-most anchor 10 from delivery device 20. Trigger 22 is then released. Torsion spring 27 rotates lever 24 clockwise and pulls piston 25 and anchor carrier 26 proximal owing to piston proximal member 33. Handle stop 34 defines the proximal position of piston 25 and anchor carrier 26 in the home state. Delivery device 20 is now reset to the home state and ready to deploy the next anchor 10.

The Method

Figure 9:
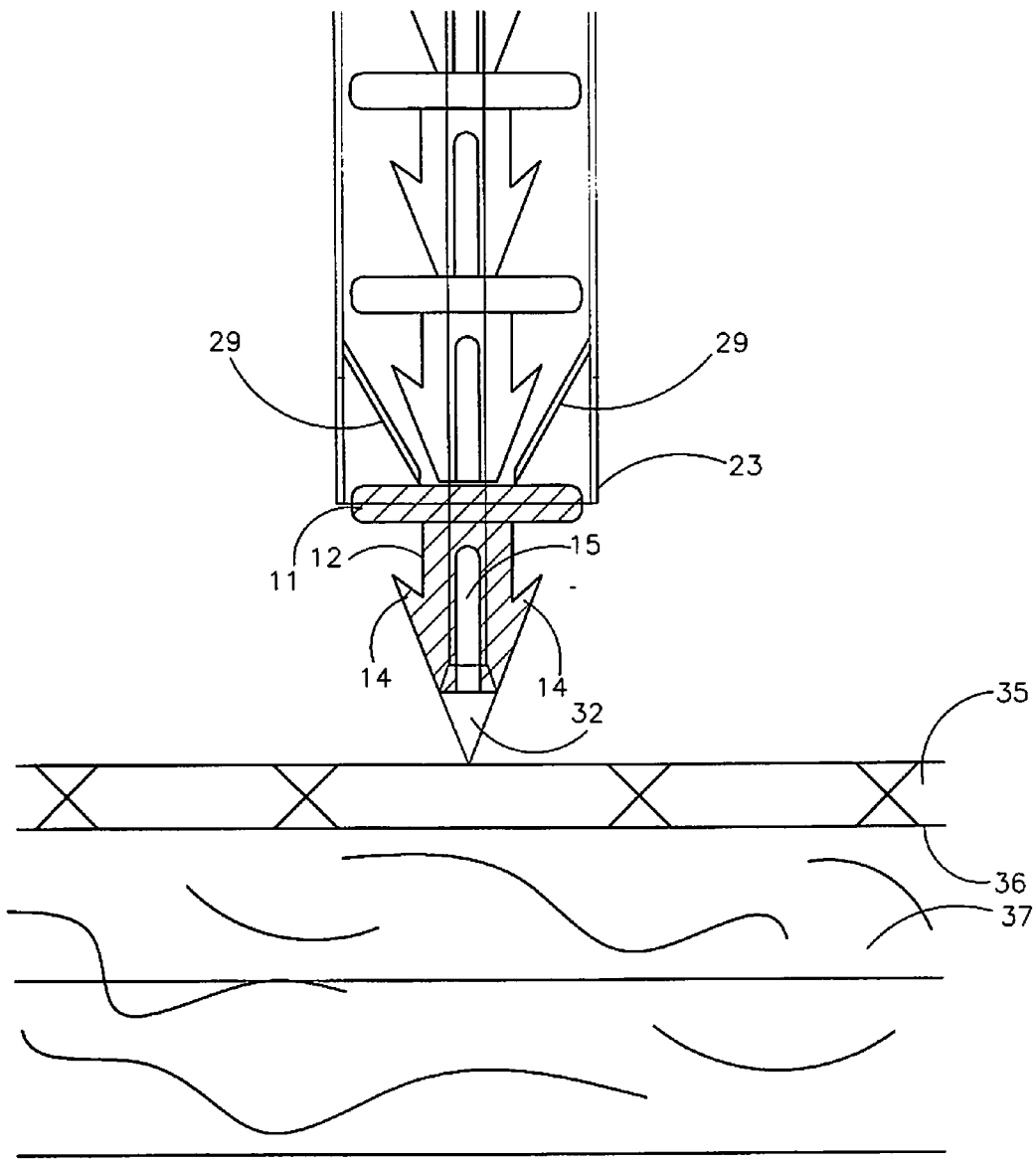
FIG. 9 depicts the deliver device in the stroked state proximate the mesh.
Figure 10:
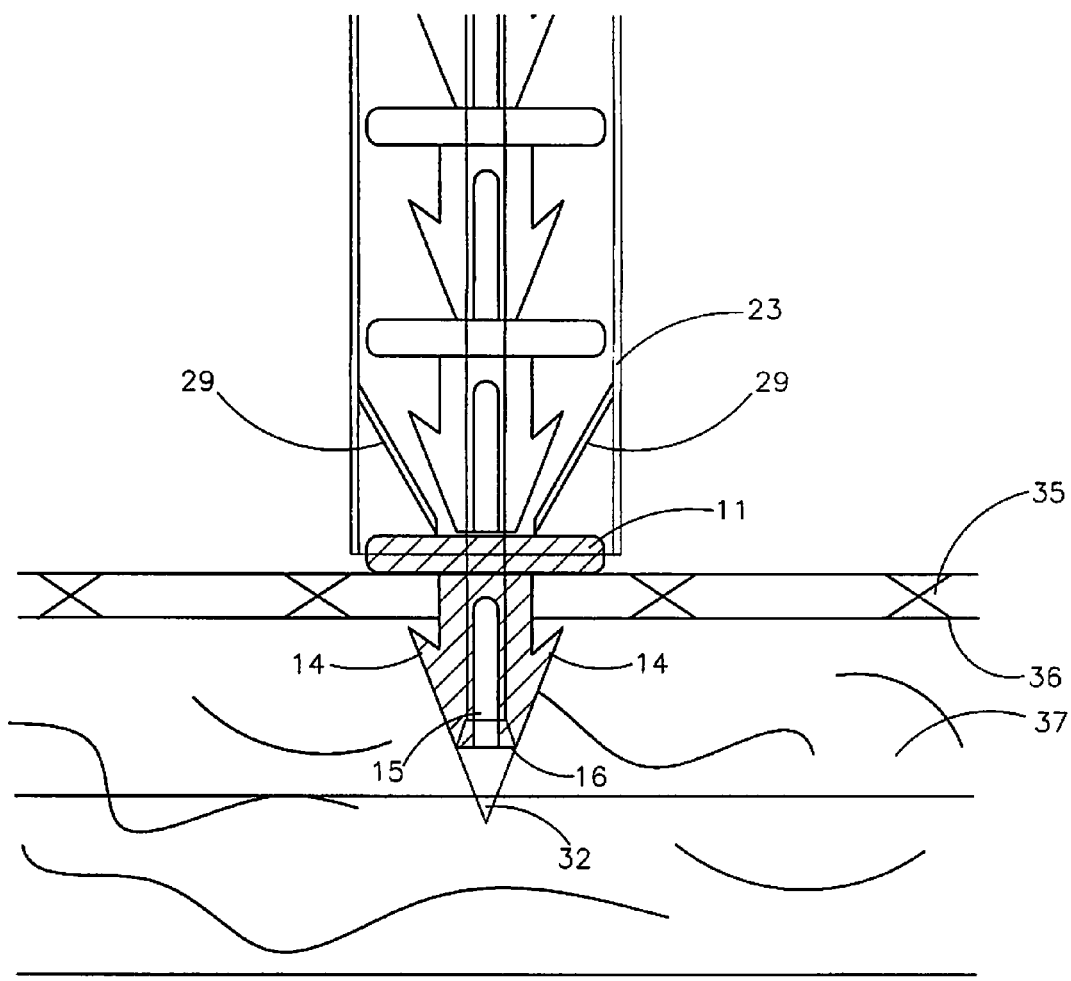
FIG. 10 shows the anchor after penetration prior to release of the trigger.
Figure 11:
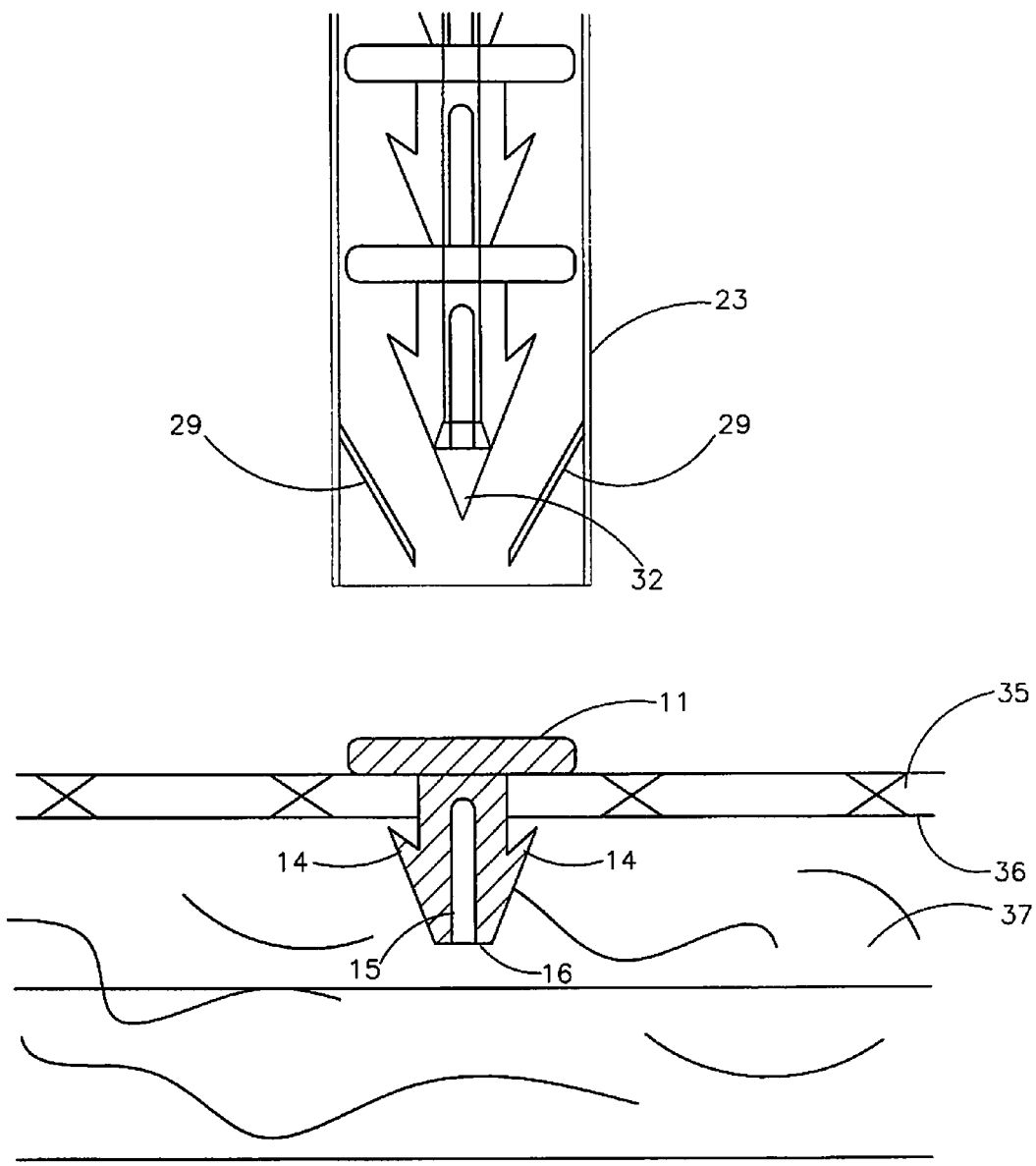
FIG. 11 shows the deployed anchor after ejection from the delivery device.

FIGS. 9-11 illustrate the method of use of the delivery device 20 and anchor 10. These longitudinal cross-sectional views of the distal end of delivery tube 23 show the steps involved in using delivery device 20 and anchor 10 for securing mesh to the inguinal floor, for example. For clarity only distal-most anchor 10 is shown crosshatched. FIG. 9 depicts the distal end of the delivery device 20 proximate mesh 35, which covers the inguinal floor 36 and underlying tissue 37. Delivery device 20 is in the fully stroked state as seen shown in detail in FIGS. 6 and 8. The surgeon has pulled trigger 22 fully proximal exposing penetrator 32, barbs 14, and penetration shaft 12 distally from delivery tube 23. The surgeon then urges the entire assembly forward so that penetrator 32 and penetration shaft 12 have penetrated mesh 35 and into tissue 37 as seen in FIG. 10. The surgeon moves delivery device 20 proximally and withdraws delivery device 10 from contact with mesh 35. Barbs 14 provide a counter force in the tissue so that anchor 10 remains in the tissue. Distal end 16 of deployed anchor 10 is flexed open owning to the counter force to torsion spring 27 so that penetrator 32 and anchor carrier 26 are allowed to move proximally through internal channel 13 of distal-most anchor 10. The surgeon then releases trigger 22. Torsion spring 27 causes lever 24 to rotate clockwise which moves piston 25 and anchor carrier 26 proximally to the home position as described above.

The proximal shoulder of penetrator 32 then nests against the next distal-most anchor so that delivery device 20 is reset to the home position and is ready for deploying another anchor 10.

While preferred embodiments of the present invention have been shown and described herein, it will be obvious to those skilled in the art that these embodiments are provided by way of example only. Numerous variations, changes, and substitutions will now occur to those skilled in the art without departing from the invention. Accordingly, it is intended that the invention be limited only by the spirit and scope of the appended claims.

The invention claimed is:

1. A method for repairing a hernia defect within a patient, the method comprising: providing a surgical anchor delivery device having a housing, a delivery tube with distal and proximal ends, a reciprocating anchor carrier, with distal and proximal ends, the distal end of the anchor carrier terminating in a tissue-penetrator member, the reciprocating anchor carrier being moveable distally and proximally with respect to the delivery device, at least one surgical anchor located in juxtaposition with the anchor carrier, a plurality of surgical anchors located within the delivery tube and radially about the anchor carrier, each surgical anchor has a penetration section and a head section; placing a prosthesis over the hernia defect and tissue adjacent thereto; exposing the penetration section of the surgical anchor beyond the distal end of the delivery tube; penetrating tissue with the tissue penetrator member and the penetration section by applying a force distally on the housing; and placing the penetration section of one of the surgical anchors through the prosthesis and within the tissue.

2. The method of claim 1 where the provided anchor is formed from one or more absorbable polymers.

3. The method of claim 1 where the provided anchor includes a blunt distal end.

4. The method of claim 1 where the provided anchor includes one or more slits for removal from the anchor carrier.

5. The method of claim 1 where the provided anchor includes one or more barbs for engagement with the tissue.

6. The method of claim 1 where the provided delivery device includes a queuing spring.

7. The method of claim 1 where the provided delivery device includes reaction members.

8. A method for repairing a hernia defect within a patient, the method comprising the steps of:

a. providing a surgical anchor delivery device having a housing, a delivery tube with distal and proximal ends, a reciprocating anchor carrier with distal and proximal ends, the distal end of the anchor carrier terminating in a tissue penetrator member, the reciprocating anchor carrier being moveable distally and proximally with respect to the delivery device, the delivery device includes a plurality of surgical anchors located radially about the anchor carrier, each surgical anchor has a penetration section and a head section;
b. placing a prosthesis over a hernia defect and a target tissue adjacent thereto;
c. placing the distal end of the delivery tube adjacent the target tissue;
d. extending the tissue penetrator member and the penetration section of a distal-most surgical anchor beyond the distal end of the delivery tube;
e. urging the device proximally to penetrate the tissue and the prosthesis with the tissue penetrator member of the anchor carrier and the penetration section of the surgical anchor.

9. The method of claim 8, further including the step of withdrawing the tissue penetrator member of the anchor carrier proximally from the target tissue and into the delivery tube.

10. The method of claim 8, wherein the provided surgical anchor delivery device includes reaction members for maintaining the distal-most surgical anchor distally beyond the distal end of the delivery tube upon withdrawal of the tissue penetrator member into the delivery tube.

11. The method of claim 8, further including the step of withdrawing the delivery device proximally to remove the distal-most surgical anchor from the anchor carrier.

12. The method of claim 8, further including the step of flexing open the distal-most surgical anchor to allow proximal movement of the tissue penetrator through an internal channel defined through the distal-most surgical anchor.

13. The method of claim 8, further including the step of nesting the tissue penetrator against a distal end of a next distal-most surgical anchor.

* * * * *